US010102343B2

(12) United States Patent
Hwang et al.

(10) Patent No.: US 10,102,343 B2
(45) Date of Patent: Oct. 16, 2018

(54) METHOD FOR EXTRACTING HEART INFORMATION BASED ON MICRO MOVEMENTS OF HUMAN BODY

(71) Applicant: SANGMYUNG UNIVERSITY SEOUL INDUSTRY-ACADEMY COOPERATION FOUNDATION, Seoul (KR)

(72) Inventors: Sung Teac Hwang, Seoul (KR); Min Cheol Whang, Gyeonggi-do (KR); Sang In Park, Seoul (KR); Dong Won Lee, Gyeonggi-do (KR)

(73) Assignee: SANGMYUNG UNIVERSITY SEOUL INDUSTRY-ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/526,784

(22) PCT Filed: Apr. 14, 2015

(86) PCT No.: PCT/KR2015/003707
§ 371 (c)(1),
(2) Date: May 15, 2017

(87) PCT Pub. No.: WO2016/080606
PCT Pub. Date: May 26, 2016

(65) Prior Publication Data
US 2017/0323072 A1 Nov. 9, 2017

(30) Foreign Application Priority Data

Nov. 18, 2014 (KR) .................. 10-2014-0160876
Nov. 18, 2014 (KR) .................. 10-2014-0160877
Feb. 3, 2015 (KR) .................. 10-2015-0016736

(51) Int. Cl.
G06K 9/00 (2006.01)
G06F 19/00 (2018.01)
(Continued)

(52) U.S. Cl.
CPC ........ *G06F 19/3418* (2013.01); *A61B 5/0077* (2013.01); *A61B 5/02028* (2013.01);
(Continued)

(58) Field of Classification Search
CPC .............. G06F 19/3418; G06F 19/321; G06K 9/00335; G06K 9/00268; A61B 5/02028;
(Continued)

(56) References Cited

U.S. PATENT DOCUMENTS 7,027,621 B1 * 4/2006 Prokoski ............ G06K 9/00248
180/272
7,431,700 B2 * 10/2008 Aoki .................... A61B 5/1135
600/529

(Continued)

FOREIGN PATENT DOCUMENTS

JP 2014171574 9/2014
JP 2014198200 10/2014
(Continued)

OTHER PUBLICATIONS

International Search Report, International Application No. PCT/KR2015/003707 dated Aug. 17, 2015.
(Continued)

Primary Examiner — John Strege
(74) Attorney, Agent, or Firm — Perman & Green, LLP

(57) ABSTRACT

A method of extracting heart information from a body micro-movement is provided. The method includes a face tracking step, a frame difference averaging step, smoothing filtering step, and a sliding peak detection step.

6 Claims, 4 Drawing Sheets

(51) Int. Cl.
*A61B 5/11* (2006.01)
*A61B 5/00* (2006.01)
*A61B 5/02* (2006.01)

(52) U.S. Cl.
CPC .......... *A61B 5/1102* (2013.01); *A61B 5/1128* (2013.01); *G06F 19/321* (2013.01); *G06K 9/00268* (2013.01); *G06K 9/00335* (2013.01); *A61B 2576/00* (2013.01)

(58) Field of Classification Search
CPC ... A61B 5/0077; A61B 5/1128; A61B 5/1102; A61B 2576/00
See application file for complete search history.

(56) References Cited

U.S. PATENT DOCUMENTS

| | | | |
|---|---|---|---|
| 2011/0251493 A1* | 10/2011 | Poh | G06K 9/00255 600/477 |
| 2011/0317874 A1* | 12/2011 | Ikenoue | G06F 3/017 382/103 |
| 2013/0135137 A1* | 5/2013 | Mulder | A61B 5/0507 342/28 |
| 2013/0250115 A1* | 9/2013 | Fan | G06K 9/00771 348/150 |
| 2013/0271591 A1* | 10/2013 | Van Leest | A61B 5/0064 348/77 |
| 2013/0296660 A1* | 11/2013 | Tsien | A61B 5/0077 600/301 |
| 2013/0331723 A1* | 12/2013 | Hernandez-Silveira | A61B 5/0816 600/529 |
| 2013/0345585 A1* | 12/2013 | Gopal Samy | A61B 5/024 600/529 |
| 2014/0303454 A1 | 10/2014 | Clifton et al. | |
| 2014/0303502 A1 | 10/2014 | Lee et al. | |
| 2014/0334697 A1 | 11/2014 | Kersten et al. | |
| 2017/0258344 A1* | 9/2017 | Seba | A61B 5/6892 |

FOREIGN PATENT DOCUMENTS

| | | |
|---|---|---|
| KR | 20060062378 | 6/2006 |
| KR | 20080054368 | 6/2008 |
| KR | 1198322 | 6/2012 |
| KR | 20140057868 | 5/2014 |
| KR | 20140058573 | 5/2014 |
| KR | 20120099111 | 7/2014 |
| KR | 20140121327 | 10/2014 |
| KR | 20140122849 | 10/2014 |
| KR | 20140124487 | 10/2014 |
| WO | 2011069021 | 6/2011 |

OTHER PUBLICATIONS

Pan, J., & Tompkins, W. J. (1985). "A Real-Time QRS Detection Algorithm." IEEE Transactions on Biomedical Engineering, BME-32(3), 230-236.
Korean Office Action, Korean Application No. 10-2015-0015567 dated Sep. 8, 2015.
Korean Office Action, Korean Application No. 10-2015-015568 dated Sep. 9, 2015.
Korean Office Action, Korean Application No. 10-2015-0017478 dated Mar. 30, 2016.
Korean Office Action, Korean Application No. 10-2015-0016735 dated Apr. 20, 2016.
Kim, C. J., et al. "A Study on Arousal Evaluation by Cardiovascular Response." Thesis paper published Nov. 2009.
Kim, M. H., et al. "Accuracy Evaluation of Measurement System Using Smartphone Camera-measured pulse of Smartphone." HCI, 2013.1, 959-961. Thesis paper published Jan. 2013.
Park, J. U. "A Study on Emotion Evaluation by Change of the Facial Micromobility." 1-96. Thesis paper published Feb. 2012.
Written Opinion of International Search Report, International Application No. PCT/KR2015/003707 dated Jan. 26, 2016.

* cited by examiner

METHOD FOR EXTRACTING HEART INFORMATION BASED ON MICRO MOVEMENTS OF HUMAN BODY

CROSS REFERENCE TO RELATED APPLICATIONS

This application is the National Stage of International Application No. PCT/KR2015/003707, having an International Filing Date of 14 Apr. 2015, which designated the United States of America, and which International Application was published under PCT Article 21 (2) as WO Publication No. 2016/080606 A1, and which claims priority from and the benefit of Korean Application No. 10-2015-0016736, filed on Feb. 3, 2015, Korean Application No. 10-2014-0160877, filed on Nov. 18, 2014, and Korean Application No. 10-2014-0160876, filed on Nov. 18, 2014, the disclosures of which are incorporated herein by reference in their entireties.

BACKGROUND

1. Field

The presently disclosed embodiment relates to methods and systems for detecting heart information (PPG) based on extraction of micro-movement information of a human body, and more particularly, to a method and system for extracting micro-movement information from a movement generated from an anatomical structure by using a non-invasive camera and extracting heart information from the micro-movement information.

2. Brief Description of Related Developments

Recently, extraction of several pieces of bio-information from a human body has been continuously studied. In particular, many researches into non-invasive bio-information acquisition and sensing techniques have been actively conducted. In particular, various researches using a wearable device and a camera are being conducted.

Micro-movements of a human body do not appear to the eye. In particular, a minute facial expression appears even when making a face, and this facial expression is referred to as a micro-expression. The micro-expression is an instantaneous and unintentional facial expression, or is instantaneously made according to an unconscious emotion or reaction state. In other words, the micro-expression is not an intentional facial expression but a movement that is made according to a biological reaction or mechanism.

In particular, a movement, shivering, and the like of such a micro-expression are used to recognize an emotional state of a human, and accordingly the micro-expression is used in implementing a feedback system (FACS).

This micro-movement of a human body appears also in parts of the body other than the face. Movements of a body cause a mechanical (instinctive/inconscious/physiological) change due to the gravity of a cardiovascular system and a respiratory system. A physical change is delivered to a central nervous system via a afferent pathway, such as a vision, a somatic sense, an autonomic nerve path, or a vestibular signal, and thus the movements of a body occur via appropriate responses to blood vessels, heartbeats, and respiratory muscles.

In particular, a vestibular system is an anatomical system that is connected to several systems of a human body and is able to keep a sense of balance, and accordingly is considered to generate movements by keeping a sense of balance about several responses. A vestibular system is controlled by various anatomical organs, such as a vestibular-oculomotor system, a vestibular-spinal system, and a vestibular-autonomic nervous system, and reacts under the influence of various organs, such as an autonomic nervous system, a cardiovascular system, and a respiratory system. Thus, a method and system for extracting bio-information as micro-movements via back-tracking of the above-described reaction of the vestibular system via a camera and extracting heartbeat information from the micro-movements is proposed.

SUMMARY

The presently disclosed embodiment provides a method of extracting micro-movement information from movements generated from an anatomical structure of a human body by using a non-invasive camera and extracting heart information (PPG) from the micro-movement information.

According to an aspect of the presently disclosed embodiment, there is provided a method of detecting heart information from a body micro-movement, the method including generating image data by photographing a micro-movement of a subject; performing face tracking on the subject while generating the image data; extracting body micro-movement information of the subject by processing the image data; performing sliding peak detection; and extracting heart information from the body micro-movement information.

According to an aspect of the presently disclosed embodiment, data of a separated space that has undergone the above-described process is amplified and is restored to the original data.

According to an aspect of the presently disclosed embodiment, the amount of entire micro-movement is extracted by calculating a difference between average movements in a previous state and a current state by calculating a difference between averages of frames of movement data of an image measured at regular intervals.

According to another aspect of the presently disclosed embodiment, there is provided a system for detecting heart information from a body micro-movement by performing the above-described method, the system including a camera configured to generate the image data; a data processor configured to process the image data from the camera; and an analyzer configured to analyze data obtained by the data processor to detect a micro-movement and detect the heart information from the micro-movement.

According to the presently disclosed embodiment, proposed is a method of extracting micro-movement information of a human body and extracting heartbeat information from the micro-movement information. According to the presently disclosed embodiment, a method of extracting micro-movement information from movements generated from an anatomical structure of a human body by using a non-invasive camera and extracting heart information (PPG) from the micro-movement information may be implemented. Recently, extraction of several pieces of bio-information from a human body has been continuously studied. In particular, many researches into non-invasive bio-information acquisition and sensing techniques have been actively conducted. In particular, various researches using a wearable device and a camera are being conducted. The micro-movement information proposed in the presently disclosed embodiment is extracted based on an anatomical basis of a human body, and is thus expected to be variously utilized in non-invasive free sensing technology as new sensing technology for extracting heart information in replacement of invasive sensing technology.

DETAILED DESCRIPTION

A heart information extracting method according to an aspect of the presently disclosed embodiment will now be described more fully with reference to the accompanying drawings.

The presently disclosed embodiment creates a moving picture of a subject or a user and extracts micro-movement data related with an internal bio-signal of the subject from the moving picture. The micro-movement data may be used as basic original data that is used to extract various pieces of body information. Heart rhythm coherence (HRC), a heart rhythm pattern (HRP), and the like may be detected from the original data, and accordingly heartbeat information of the subject, for example, may be extracted.

Figure 1:
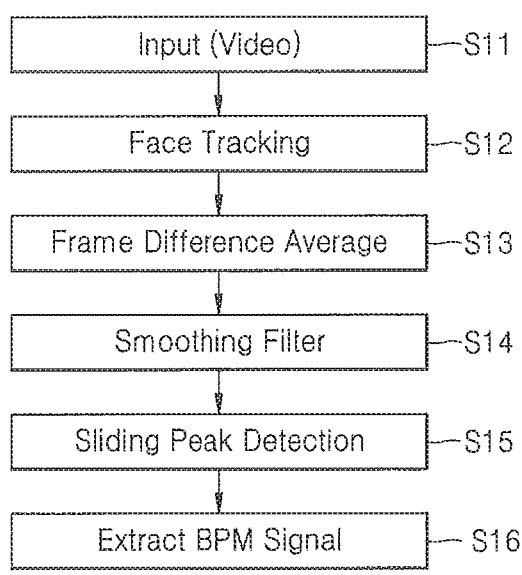
FIG. 1 is a flowchart of a method of extracting heart information, according to the presently disclosed embodiment.
Figure 2:
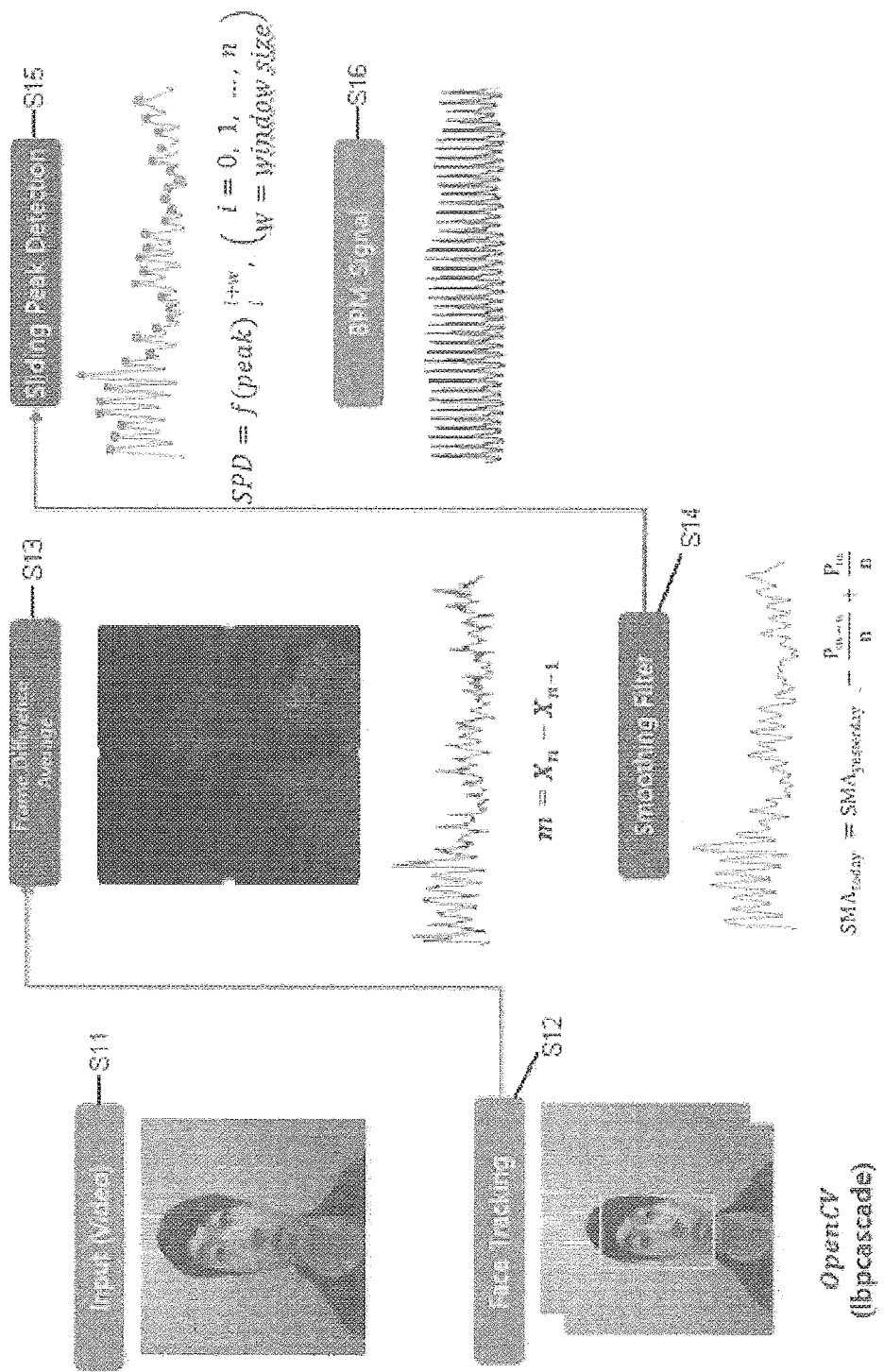
FIG. 2 illustrates an operational scenario of the steps of FIG. 1.

A method of extracting micro-movement data according to the presently disclosed embodiment includes a total of six steps as shown in FIG. 1. FIG. 2 illustrates an operational scenario of the steps of FIG. 1.

A. Video Input Step S11

A subject is photographed by a video camera, and thus consecutive image data is generated. At this time, an upper body including the face of the subject is photographed, as shown in FIG. 2.

B. Face Tracking Step S12

To extract micro-movements of the human body from the head by using the image data received via the video camera, image information is separated via facial recognition using an open computer vision (OpenCV).

The OpenCV is an open source computer vision C library. The OpenCV was originally developed by Intel and may be used in several platforms, such as Windows and Linux. The OpenCV is a library focused on real-time image processing.

A facial recognition system based on the OpenCV refers to a computer-assisted application program that automatically identifies each person via a digital image. This is achieved by comparing a selected face feature appearing on a real-time image with a face database.

In FIG. 2, in step S12, a rectangle on the original image indicates a tracking region of a face part. Tracking is performed on the face part according to a movement of the user.

C. Frame Difference Average Step S13

A difference m between average movements Xn and Xn−1 in a previous state and a current state is calculated by calculating a difference between averages of frames of movement data of an image measured at regular intervals (30 fps), thereby extracting the amount of the entire micro-movement from separated image information. The average of one frame indicates the amount m of a micro-movement of one frame.

$$m = X_n - X_{n-1} \qquad \text{[Equation 1]}$$

D. Smoothing Filtering Step S14

When the extracted micro-movement is extracted as data, noise with respect to the movement is included in the extracted data, and thus a signal is roughly distorted, making peak detection difficult. Accordingly, data that removes noise and increases the accuracy of peak detection is processed.

$$SMA = \frac{P_m + P_{m-1} + \ldots + P_{m-(n-1)}}{n} \qquad \text{[Equation 2]}$$

$$SMA_{today} = SMA_{yesterday} - \frac{P_{m-n}}{n} + \frac{P_m}{n} \qquad \text{[Equation 3]}$$

where SMA indicates a moving average value, SMAtoday and SMAyesterday indicate moving average values on different specific dates, Pm indicates a value of a micro-movement of a current frame, and n indicates a window size of a moving average.

E. Sliding Peak Detection Steps S15 and S16

Peak data per frame continuously slides based on windows of a size of 30 seconds by receiving processed data for removing noise and detecting a peak, thereby minimizing a movement effect and an effect upon data and thus enabling a bit per minute (BPM) signal to be extracted.

$$SPD = f(\text{peak})_i^{i+w}, \begin{pmatrix} i = 0, 1, \ldots, n \\ w = \text{window size} \end{pmatrix} \qquad \text{[Equation 4]}$$

A PPG signal obtained in the above process detected an R-peak via a QRS detection algorithm (Pan and Tompkins, 1985). Noise component is removed from the detected R-peak data and a R-peak to R-peak interval (RRI) is extracted by using a difference of a normal R-peak interval. A BPM may be calculated via 60/RRI in order to analyze an HRP, and a standard deviation normal to normal (SDNN) may be extracted using a standard deviation of the normal RRI.

A function implemented as in the flowchart of FIG. 1 and actually processed enables average data of a final micro-movement to be extracted as shown in FIG. 2.

Figure 4:
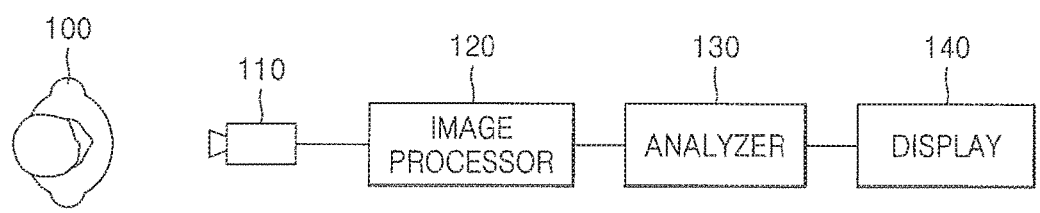
FIG. 4 is a schematic block diagram of a heart information extracting system according to an aspect of the presently disclosed embodiment.

FIG. 4 is a schematic block diagram of a micro-movement extracting system according to the presently disclosed embodiment.

A moving picture obtained by a webcam or compact video camera 110 facing a subject 100 passes through an image processor 120, and thus a specific image is extracted from the moving picture. The specific image is processed by a processing device 130. The processing device 130 has software for performing a method as described above, and a hardware system that supports the software. The processing device 130 may be a computer-based device, for example, a general-purpose computer or dedicated device including software that contains a method or algorithm as described above and hardware that is driven by the software.

A processing result from the processing device 130 is displayed on a display 140. Such a system may further include a general external interface device, for example, a keyboard or a mouse, including a general input.

Verifying Method

<Subject>

10 university students (5 men and 5 women) were classified into subjects with an expressionless face and subjects showing an expression on their faces and participated in two experiments. All of the subjects had no disorders or no medical histories in a heart's-blood nervous system and were advised to take sufficient sleeps on the previous date. Moreover, caffeine intake, smoking, and drinking that may affect a reaction of a cardiovascular system were prohibited on the day before the experiment. Before the experiment is conducted, general matters about the experiment except for the research purpose were explained to all of the subjects, and the subjects were paid a certain amount of money for participation in the experiment.

<Experiment Method>

An expressionless-face experiment when subjects have blank expressions on their faces and an expressive-face experiment when subjects show expressions on their faces along a suggested stimulus of a facial expression were conducted. In this case, facial expression stimuli for six basic emotions (fear, disgust, sadness, surprise, anger, and happiness) of Ekman were equally suggested such that the subjects make facial expressions. While the experiment was being conducted, subjects wore PPG sensors and, simultaneously, images of the upper bodies of the subjects were measured. The measurement was conducted for three minutes for the expressionless-face experiment, and the measurement was conducted for three minutes for the expressive-face experiment.

<Analysis Method>

A PPG signal was sampled at 500 Hz via a lead-I method. An electrocardiogram signal was obtained by amplifying a signal via a MP100 power supply and a PPG 100C amplifier (Biopac systems Inc., USA) and converting an analog signal into a digital signal via NI-DAQ-Pad9205 (National instruments, USA). The PPG signal underwent peak detection via Sliding Peak Detection, and an image signal underwent peak detection via a micro-movement extraction method. For statistical verification between two different signals, signal processing was conducted on the two different signals under the same condition that a window size is 30. Data respectively extracted after the two different signals are processed underwent a correlation analysis via SPSS 17.0 K, and thus correlation coefficients were induced.

<Analysis Result>

A correlation analysis was conducted on respective data of 10 subjects by using information extracted by using a PPG sensor and information extracted from a micro-movement, and, as a result, correlation coefficient average values of the 10 subjects were high in the expressionless-face experiment (r=0.89, SD=0.054, p<0.05). During an expressive-face experiment capable of affecting movements of the same 10 subjects, the 10 subjects had correlation coefficients that are slightly lower than the case of the expressionless-face experiment but are still high (r=0.74, SD=0.087, p<0.05).

Table 1 below shows a result of the correlation analysis.

TABLE 1

| Participants | Expressionless face r | Expressive face r |
|---|---|---|
| P1 | 0.729 | 0.729 |
| P2 | 0.618 | 0.618 |
| P3 | 0.732 | 0.532 |
| P4 | 0.726 | 0.626 |
| P5 | 0.702 | 0.62 |
| P6 | 0.682 | 0.582 |
| P7 | 0.746 | 0.546 |
| P8 | 0.592 | 0.592 |
| P9 | 0.786 | 0.786 |
| P10 | 0.668 | 0.468 |
| Avg. | 0.6981 | 0.6081 |
| SD | 0.056353261 | 0.087713682 |

Figure 3:
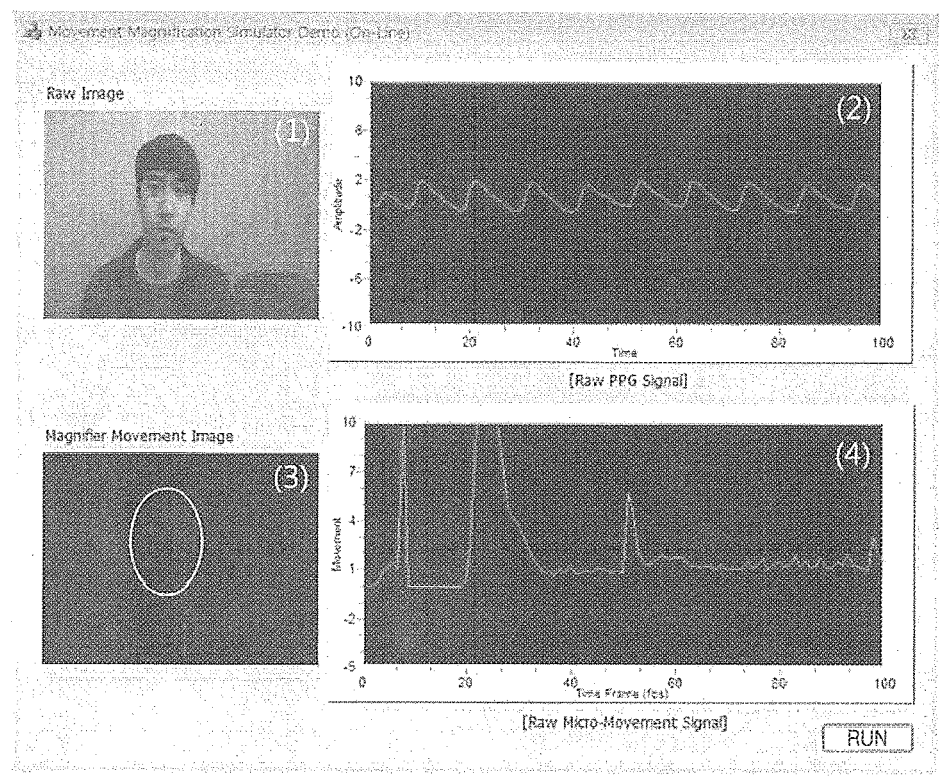
FIG. 3 illustrates a screen structure of a program for extracting heart information, according to the presently disclosed embodiment.

FIG. 3 illustrates an example of a screen image of a heartbeat information extraction program as a program (interface) that shows an implementation result.

According to the aspect shown in FIG. 3, a screen image showing an image of an upper body of a human body, which is above a breast, and showing that data of an actual original image is being operated is illustrated.

FIG. 3 also illustrates a graph image for showing a PPG signal obtained using a PPG amplifier and a sensor manufactured by Biopac and comparing a micro-movement with a raw PPG signal.

In FIG. 3, an image in a line shape generated by amplifying a micro-movement not appearing on an actual difference image from the data of the original image operating in (1) via micro-movement extraction technology is illustrated, and only a portion that moved in a line shape when a portion outlined in a circle actually minutely moved is shown.

Furthermore, in the screen image of FIG. 3, data obtained by amplifying a micro-movement is represented in a data graph such that information about a movement may be displayed in real time.

While the presently disclosed embodiment has been particularly shown and described with reference to exemplary aspects thereof, it will be understood by those of ordinary skill in the art that various changes in form and details may made therein without departing from the spirit and scope as defined by the following claims.

What is claimed is:

1. A method of detecting heart information from a body micro-movement, the method comprising:
    generating image data by photographing a micro-movement of a subject;
    performing face tracking on the subject while generating the image data;
    extracting body micro-movement information of the subject by processing the image data;
    performing sliding peak detection; and
    extracting heart information from the body micro-movement information
    wherein the extracting of the body micro-movement information comprises extracting an amount of an entirety of the micro-movement by calculating a difference between average movements in a previous state and a current state by calculating a difference between average of frames of movement data of an image measured at regular intervals.

2. The method of claim 1, wherein the body micro-movement information undergoes smoothing filtering to increase accuracy of peak detection.

3. A system for detecting heart information from a body micro-movement by performing the method of claim 1, the system comprising:

a camera configured to generate the image data;

a data processor configured to process the image data from the camera; and an analyzer configured to analyze data obtained by the data processor to detect a micro-movement and detect the heart information from the micro-movement.

4. The system of claim 3, wherein the analyzer is configured to also perform smoothing filtering to remove noise from the body micro-movement information, before performing the sliding peak detection.

5. A system for detecting heart information from a body micro-movement by performing the method of claim 2, the system comprising:

a camera configured to generate the image data;

a data processor configured to process the image data from the camera; and an analyzer configured to analyze data obtained by the data processor to detect a micro-movement and detect the heart information from the micro-movement.

6. The system of claim 5, wherein the analyzer is configured to also perform smoothing filtering to remove noise from the body micro-movement information, before performing the sliding peak detection.

* * * * *